United States Patent [19]

Hatfield et al.

[11] Patent Number: 5,779,641
[45] Date of Patent: Jul. 14, 1998

[54] METHOD AND APPARATUS FOR THREE-DIMENSIONAL ULTRASOUND IMAGING BY PROJECTING FILTERED PIXEL DATA

[75] Inventors: William Thomas Hatfield; Harvey E. Cline, both of Schenectady, N.Y.

[73] Assignee: General Electric Company, Schenectady, N.Y.

[21] Appl. No.: 852,773

[22] Filed: May 7, 1997

[51] Int. Cl.⁶ .................................................. A61B 8/00
[52] U.S. Cl. ........................................... 600/443; 128/916
[58] Field of Search .............................. 600/443, 454, 600/455, 447, 456, 437

[56] References Cited

U.S. PATENT DOCUMENTS

| | | | |
|---|---|---|---|
| 5,159,931 | 11/1992 | Pini | 600/443 |
| 5,226,113 | 7/1993 | Cline et al. | 395/124 |
| 5,241,371 | 8/1993 | Ohba | 358/22 |
| 5,282,471 | 2/1994 | Sato | 600/443 |
| 5,327,894 | 7/1994 | Thomas | 600/454 |
| 5,365,929 | 11/1994 | Peterson | 128/661.1 |
| 5,409,007 | 4/1995 | Saunders et al. | 600/447 |
| 5,474,073 | 12/1995 | Schwartz et al. | 128/661.1 |
| 5,485,842 | 1/1996 | Quistgaard | 128/660.07 |
| 5,566,674 | 10/1996 | Weng | 600/443 |
| 5,582,173 | 12/1996 | Li | 128/660.07 |
| 5,582,176 | 12/1996 | Swerling et al. | 600/455 |
| 5,601,084 | 2/1997 | Sheehan et al. | 600/443 |
| 5,655,535 | 8/1997 | Friemel et al. | 128/660.07 |

FOREIGN PATENT DOCUMENTS

WO 97/00482   1/1997   WIPO

*Primary Examiner*—Marvin M. Lateef
*Assistant Examiner*—Maulin Patel
*Attorney, Agent, or Firm*—Dennis M. Flaherty; John H. Pilarski

[57] ABSTRACT

A method and an apparatus for three-dimensional imaging of ultrasound data by reducing speckle artifact data before the acquired data from a volume of interest is projected onto an image plane. An ultrasound scanner collects B-mode or color flow mode images in a cine memory, i.e., for a multiplicity of slices. The data from a respective region of interest for each slice is sent to a master controller, such data forming a volume of interest. The master controller performs an algorithm that iteratively projects the pixel data in the volume of interest onto a plurality of rotated image planes using a ray-casting technique. Prior to projection, the master controller smooths the speckle contained in the pixel data filtering using a convolution filter having a nine-point kernel. Convolution filtering of image data is carried out by defining a desired area of the image, such as an area represented by an array of pixels, by weighting each of the pixels in the array with a respective weighting coefficient, and then by summing the weighted pixels to produce a filtered pixel value which is substituted for the central pixel in the array. The filtered pixel data forms a new data volume which is then projected onto each successive image plane.

18 Claims, 8 Drawing Sheets

| $DV_{4,4,1}$ | $DV_{3,4,1}$ | $DV_{2,4,1}$ | $DV_{1,4,1}$ |
|---|---|---|---|
| $DV_{4,3,1}$ | $DV_{3,3,1}$ | $DV_{2,3,1}$ | $DV_{1,3,1}$ |
| $DV_{4,2,1}$ | $DV_{3,2,1}$ | $DV_{2,2,1}$ | $DV_{1,2,1}$ |
| $DV_{4,1,1}$ | $DV_{3,1,1}$ | $DV_{2,1,1}$ | $DV_{1,1,1}$ |

FIG. 7A

| $W_1$ | $W_2$ | $W_3$ |
|---|---|---|
| $W_4$ | $W_5$ | $W_6$ |
| $W_7$ | $W_8$ | $W_9$ |

FIG. 7B

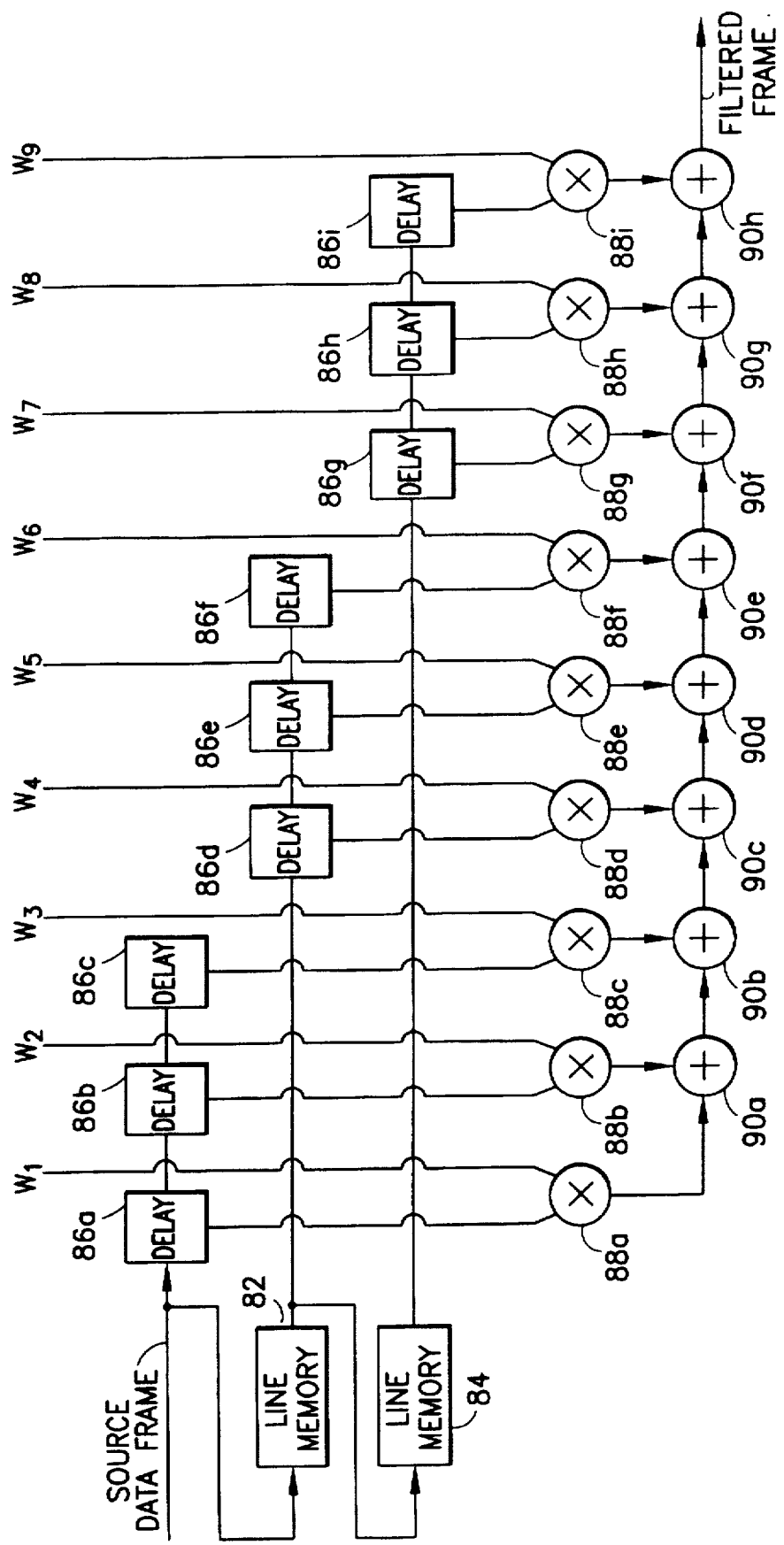

METHOD AND APPARATUS FOR THREE-DIMENSIONAL ULTRASOUND IMAGING BY PROJECTING FILTERED PIXEL DATA

FIELD OF THE INVENTION

This invention generally relates to ultrasound imaging of the human anatomy for the purpose of medical diagnosis. In particular, the invention relates to a method and an apparatus for three-dimensional imaging of blood vessels in the human body by detecting the intensity of ultrasonic echoes reflected from the vessel.

BACKGROUND OF THE INVENTION

The most common modes of diagnostic ultrasound imaging include B- and M-modes (used to image internal, physical structure), Doppler, and color flow (the latter two primarily used to image flow characteristics, such as in blood vessels). In conventional B-mode imaging, ultrasound scanners create images in which the brightness of a pixel is based on the intensity of the echo return. The color flow mode is typically used to detect the velocity of fluid flow toward/away from the transducer, and it essentially utilizes the same technique as is used in the Doppler mode. Whereas the Doppler mode displays velocity versus time for a single selected sample volume, color flow mode displays hundreds of adjacent sample volumes simultaneously, all superimposed on a B-mode image and color-coded to represent each sample volume's velocity.

Measurement of blood flow in the heart and vessels using the Doppler effect is well known. Whereas the amplitude of the reflected waves is employed to produce black and white images of the tissues, the frequency shift of backscattered waves may be used to measure the velocity of the backscatterers from tissue or blood. The change or shift in backscattered frequency increases when blood flows toward the transducer and decreases when blood flows away from the transducer. Color flow images are produced by superimposing a color image of the velocity of moving material, such as blood, over the black and white anatomical image. The measured velocity of flow at each pixel determines its color.

The advantage of displaying B-mode anatomical data around velocity data is that more useful information is provided to the user than is provided when velocity data is presented with an opaque background. Also, it is easier for the user to find the anatomy to be scanned without having to turn: off the velocity capability.

The present invention is incorporated in an ultrasound imaging system consisting of four main subsystems: a beamformer 2 (see FIG. 1), processor subsystem 4, a scan converter/display controller 6 and a master controller 8. System control is centered in master controller 8, which accepts operator inputs through an operator interface (not shown) and in turn controls the various subsystems. The master controller also generates the system timing and control signals which are distributed via a system control bus 10 and a scan control bus (not shown).

The main data path begins with the digitized RF inputs to the beamformer from the transducer. The beamformer outputs two summed digital baseband receive beams. The baseband data is input to B-mode processor 4A and color flow processor 4B, where it is processed according to the acquisition mode and output as processed acoustic vector (beam) data to the scan converter/display controller 6. The scan converter/display controller 6 accepts the processed acoustic data and outputs the video display signals for the image in a raster scan format to a color monitor 12. The scan converter/display controller 6, in cooperation with master controller 8, also formats multiple images for display, display annotation, graphics overlays and replay of cine loops aid recorded timeline data.

The B-mode processor 4A converts the baseband data from the beamformer into a log-compressed version of the signal envelope. The B function images the time-varying amplitude of the envelope of the signal as a grey scale using an 8-bit output for each pixel. The envelope of a baseband signal is the magnitude of the vector which the baseband data represent.

The frequency of sound waves reflecting from the inside of blood vessels'heart cavities, etc. is shifted in proportion to the velocity of the blood cells: positively shifted for cells moving towards the transducer and negatively for those moving away. The color flow (CF) processor 4B is used to provide a real-time two-dimensional image of blood velocity in the imaging plane. The blood velocity is calculated by measuring the phase shift from firing to firing at a specific range gate. Instead of measuring the Doppler spectrum at one range gate in the image, mean blood velocity from multiple vector positions and multiple range gates along each vector are calculated, and a two-dimensional image is made from this information. More specifically, the color flow processor produces velocity (8 bits), variance (turbulence) (4 bits) and power (8 bits) signals. The operator selects whether the velocity and variance or power are output to the scan converter. The output signal is input to a chrominance control lookup table which resides in the video processor 22. Each address in the lookup table stores 24 bits. For each pixel in the image to be produced, 8 bits control the intensity of red, 8 bits control the intensity of green and 8 bits control the intensity of blue. These bit patterns are preselected such that as the flow velocity changes in direction or magnitude, the color of the pixel at each location is changed. For example, flow toward the transducer is indicated as red and flow away from the transducer is indicated as blue. The faster the flow, the brighter the color.

The acoustic line memories 14A and 14B of the scan converter/display controller 6 respectively accept processed digital data from processors 4A and 4B and perform the coordinate transformation of the color flow and B-mode data from polar coordinate (R-θ) sector format or Cartesian coordinate linear array to appropriately scaled Cartesian coordinate display pixel data stored in X-Y display memory 18. In the B-mode, intensity data is stored X-Y display memory 18, each address storing three 8-bit pixels. Alternatively, in the color flow mode, color flow data is stored in memory as follows: intensity data (8 bits), velocity or power data (8 bits) and turbulence data (4 bits). A multiplicity of successive frames of color flow or B-mode data are stored in cine memory on a first-in, first out basis. The cine memory is like a circular image buffer that runs in the background, continually capturing image data that is displayed in real time to the user. When the user freezes the system, the user has the capability to view image data previously captured in cine memory. The graphics data for producing graphics overlays on the displayed image is generated and stored in the timeline/graphics processor and display memory 20. The video processor 22 multiplexes between the graphics data, image data, and timeline data to generate the final video output in a raster scan format on video monitor 12. Additionally it provides for various greyscale and color maps as well as combining the greyscale and color images.

The conventional ultrasound imaging system collects B-mode or color flow mode images in a cine memory 24 on a continuous basis. The cine memory 24 provides resident digital image storage for single image review and multiple image loop review and various control functions. The region of interest displayed during single-image cine replay is that used during the image's acquisition. The cine memory also acts as a buffer for transfer of images to digital archival devices via the master controller 8.

Conventional ultrasound scanners create two-dimensional B-mode images in which the brightness of a pixel is based on the intensity of the echo return. In color flow imaging, if movement is present, a Doppler shift in the return signal is produced proportional to the speed of movements. For instance. blood flowing in an artery will produce a Doppler shift. The Doppler shift may be displayed using different colors to represent speed and direction of flow. Flow toward the transducer is typically shown in red, while flow away from the transducer is shown in blue. In power Doppler imaging, the power contained in the returned Doppler signal is displayed.

Two-dimensional ultrasound images are often hard to interpret due to the inability of the observer to visualize the two-dimensional representation of the anatomy being scanned. However, if the ultrasound probe is swept over an area of interest and two-dimensional images are accumulated to form a three-dimensional volume, the anatomy becomes much easier to visualize for both the trained and untrained observer. Typically, three-dimensional images of B-mode data and color flow velocity or power data are displayed separately. However, there are many occasions when, by displaying velocity or power data alone, the viewer loses a sense of the anatomy being imaged. By combining intensity projections with projections of color flow velocity or power data, it is possible to retain a sense of the anatomy and at the same time image the velocity or power. This gives the viewer a sense of how the vascularity represented by color flow imaging may be associated with a portion on the anatomy such as a tumor or cyst. Three-dimensional ultrasound imaging is particularly useful in visualizing blood vessels during vascular procedures or open surgery of the liver.

Ultrasound imaging suffers from the inherent imaging artifact referred to as speckle. Speckle is the mottling found in the images produced from interference patterns of multiple receive echoes. This mottling is primarily caused by the null in the acoustic interference pattern, but other anomalies in the image, e.g., random electronic noise, can cause mottling. The acoustic nulls are accentuated by the log compression required to display the full dynamic range of the ultrasound image. These nulls appear as black holes in the image. Speckle noise and artifacts limit the range of acceptable view angles in three-dimensional ultrasound imaging.

Since any parameter which changes the sum of the returning echoes will alter the speckle pattern, a number of conventional methods exist for reducing the speckle image artifact. Examples of such conventional methods include multiple transmit focusing, spatial compounding, frequency compounding and spatial low-pass filtering. The multiple transmit focusing, spatial compounding and frequency compounding techniques suffer from reduced frame rates, whereas spatial low-pass filtering has reduced resolution.

SUMMARY OF THE INVENTION

The present invention is a method and an apparatus for three-dimensional imaging of ultrasound data by reducing speckle artifact data before the acquired data from a volume of interest is projected onto an image plane. The apparatus comprises an ultrasound scanner which collects B-mode or color flow mode images in a cine memory on a continuous basis or in response to an external trigger event, i.e., for a multiplicity of slices. The data from a respective region of interest for each slice is sent to a master controller, such data forming a volume of interest. The master controller performs an algorithm that iteratively projects the pixel data in the volume of interest onto a plurality of rotated image planes using a ray-casting technique.

In accordance with the invention, prior to carrying out the projection algorithm, the master controller smooths the speckle and/or noise contained in the pixel data by filtering. This filtering is performed by stepping a nine-point kernel through the pixel data in each region of interest retrieved from the two-dimensional slices making up the data volume of interest.

In accordance with the preferred embodiment of the invention, a convolution filter is used to smooth speckle in the pixel data. In particular, each two-dimensional region of interest read from the cine memory is convolution filtered in two dimensions, i.e., the pixel data is filtered in both the horizontal and vertical directions.

Convolution filtering of image data is carried out by defining a desired area of the image, such as an area represented by an n×n array of pixels (where n≧2), by weighting each of the pixels in the n×n array with a respective weighting coefficient, and then by summing the weighted pixels to produce a filtered pixel value which is substituted for one of the pixels in the n×n array, e.g., the central pixel in a 3×3 array. Alternatively, the volume of interest can be filtered using a convolution filter having an n×n×n kernel. Convolution filtering can be implemented by digital filter techniques. Alternatively, the pixel data can be filtered using a median filter or an edge-preserving filter.

The filtered pixel data forms a new data volume which is then projected onto each successive image plane. The projected images having reduced speckle and noise are stored as separate frames in the cine memory, each frame being superimposed on the last background frame. These reconstructed frames are then displayed selectively by the system operator. The images clearly show any blood vessels in the object volume. When shown in the cine mode, the vessels rotate and a greater sense of depth perception is obtained as compared to that achieved by imaging a two-dimensional slice.

BRIEF DESCRIPTION OF THE DRAWINGS

FIG. 7A is a schematic depicting a two-dimensional array of pixel data.

FIG. 7B is a schematic depicting a 3×3 set of weighting coefficients which are used by the convolution filter in accordance with the present invention.

FIG. 8 is a schematic block diagram of a convolution filter in accordance with a preferred embodiment of the invention.

DETAILED DESCRIPTION OF THE PREFERRED EMBODIMENTS

Figure 2:
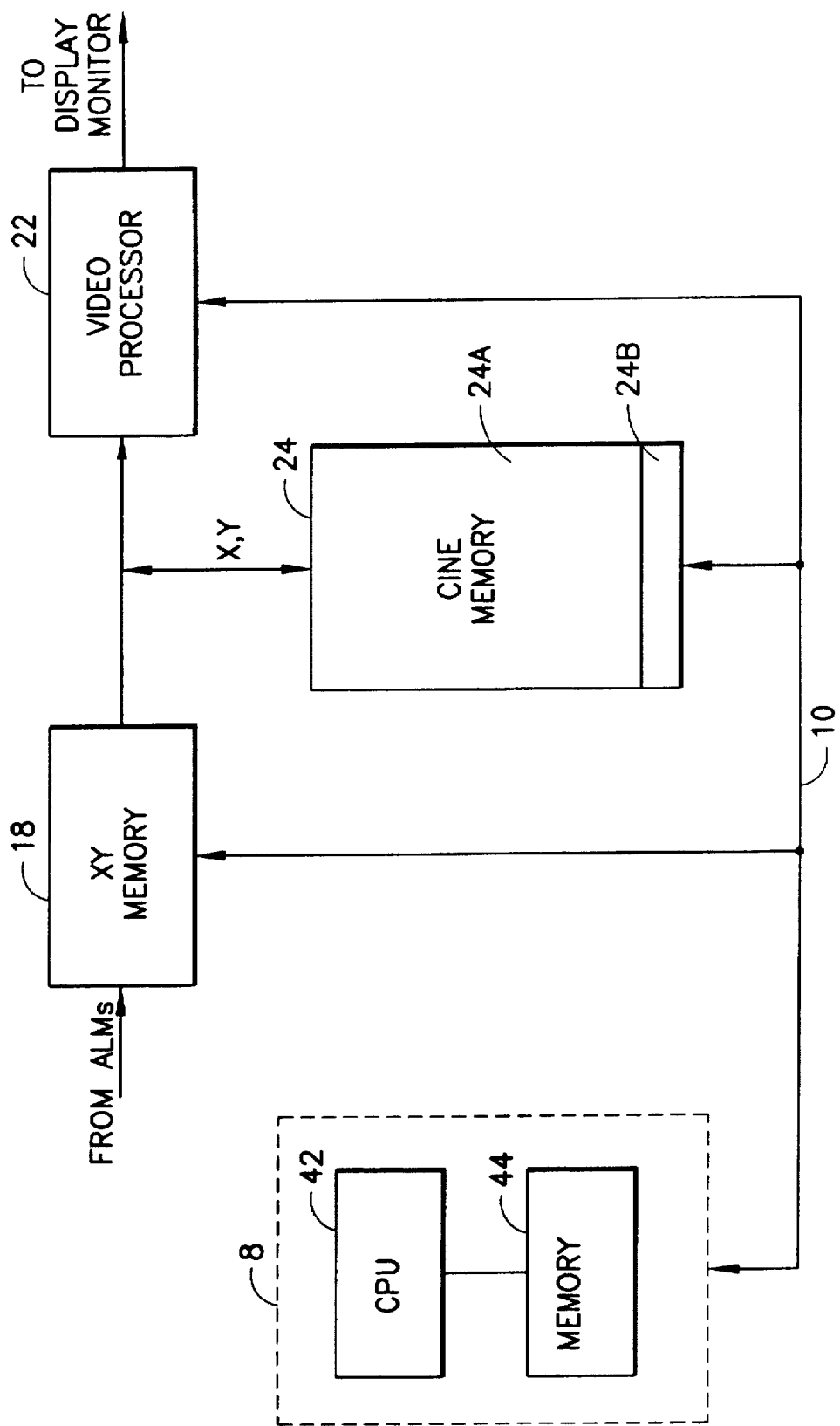
FIG. 2 is a block diagram showing the means for reconstructing frames comprising successive volumetric projections of intensity and velocity or power pixel data in accordance with a preferred embodiment of the present invention.

Referring to FIG. 2, the master controller 8 comprises a central processing unit (CPU) 42 and a random access memory 44. The CPU 42 has read only memory incorporated therein for storing routines used in transforming the acquired volume of intensity or color flow mode data into a multiplicity of three-dimensional projection images taken at different angles. The CPU 42 controls the XY memory 18 and the cine memory 24 via the system control bus 10. In particular, the CPU 42 controls the flow of pixel data from the XY memory 18 to the video processor 22 and to the cine memory 24, and from the cine memory to the video processor 22 and to the CPU 42 itself. When the ultrasound imaging system is operating in the color flow mode, each frame of color flow data, representing one of a multiplicity of parallel scans or slices through the object being examined, is stored in the XY memory 18 and in the next cycle is transmitted to video processor 22 and to cine memory 24. A stack of frames, representing the scanned object volume, is stored in section 24A of cine memory 24. During initialization (see step 26 in FIG. 3), the CPU 42 retrieves from cine memory section 24A only the color flow data corresponding to an object volume of interest. This is accomplished by retrieving only the color flow data in a region of interest from each stored frame acquired from any scan which intersected the object volume of interest. In other words, the color flow data corresponding to the region of interest from each one of a stack of successive frames forms a source data volume of interest.

Figure 3:
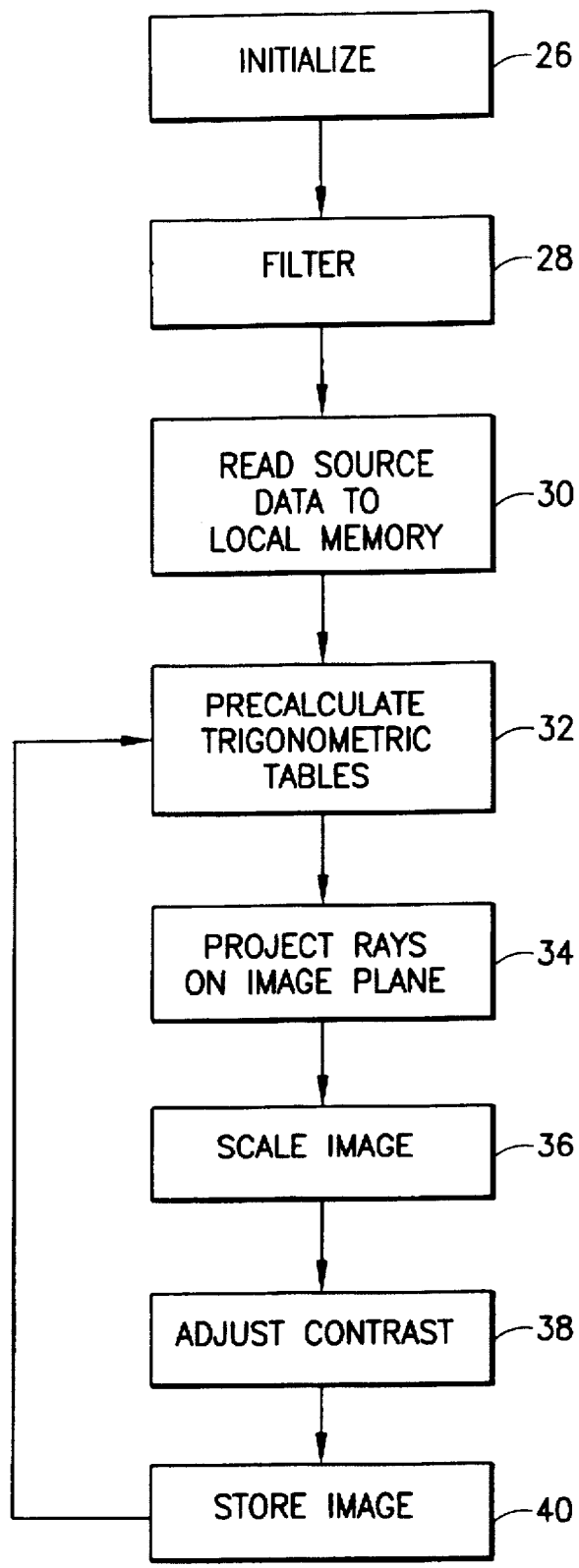
FIG. 3 is a flowchart showing the steps of an algorithm for reconstructing frames comprising successive volumetric projections of intensity and velocity or power pixel data in accordance with the preferred embodiment of the present invention.

As seen in FIG. 3, the intensity data in the pixel data set corresponding to the object volume of interest is filtered (step 28) prior to projection in order to smooth speckle noise and reduce artifacts. This prevents the loss of data due to speckle noise during projection. For example, blood vessels are less echogenic than the surrounding tissue. Therefore vessels can be imaged using minimum intensity projections. Alternatively, in the reverse video/minimum mode, the intensity data is inverted to make the vessels bright instead of dark. The vessels can then be imaged using maximum intensity projections. To prevent the selection of maximum intensities which are bright speckle as opposed to desired pixel data, a filter can be used to remove such bright speckle intensities prior to projection. In accordance with the preferred embodiment of the invention, the pixel data retrieved from the cine memory 24 (see FIG. 2) is filtered by CPU 42 using a 3×3 convolution filter having a 111 141 111 kernel, i.e., the central pixel of intensity data in each 3×3 pixel array in each slice or frame is replaced by an intensity value proportional to the sum of four times the value of the central pixel plus the sum of the values of the eight pixels surrounding that pixel. The filtered source data volume is then stored in memory 44 (step 30). In a similar manner, a convolution filter can be used to remove black holes in an image prior to minimum intensity projection.

Next the CPU 42 performs a series of transformations using the ray casting algorithm disclosed in U.S. Pat. No. 5,226,113. The successive transformations represent maximum, minimum or averaged intensity, velocity or power projections made at angular increments, e.g., at 10° intervals, within a range of angles, e.g., +90° to −90°. However, the angular increment need not be 10°; nor is the invention limited to any particular range of angles.

Figure 4:
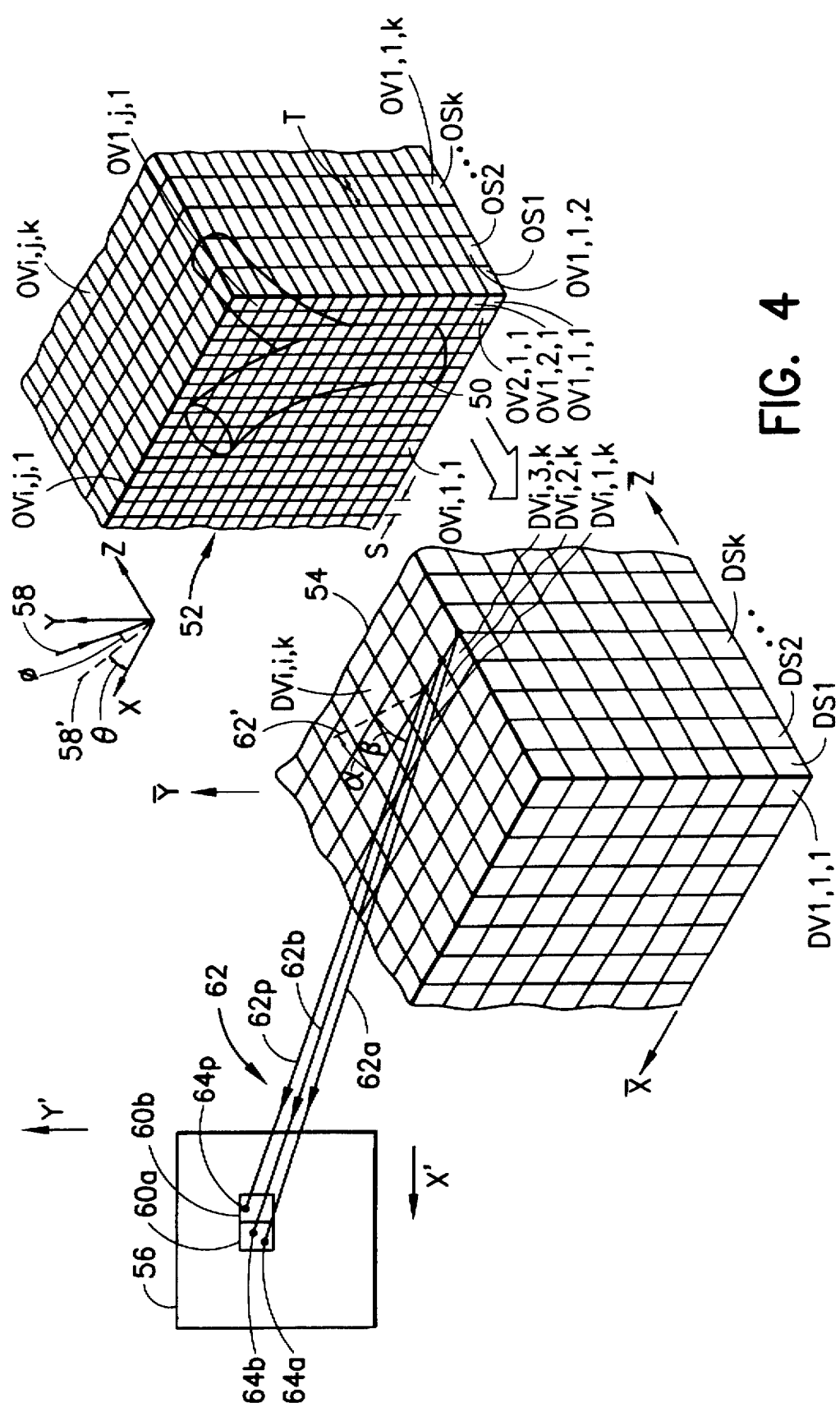
FIG. 4 is a schematic of the sampled object volume of interest, an associated data volume and an image projection plane involved in volumetrically rendering a reversed raycast projection in accordance with the prior art.

In accordance with the ray casting technique employed in the present invention, volumetrically rendered projection images of a sample 50 (see FIG. 4) is displayed from any arbitrary viewing angle, e.g. a spherical projection angle denoted by angle parameters $(\theta,\phi)$, where $\theta$ is the angle that an extension 58' of a viewing ray 58 makes upon the X-Y plane, and $\phi$ is the angle of ray 58 with respect to extension 58', by scanning an object volume 52 an ultrasound transducer. Sample volume 52 is scanned in such a manner as to create a series of stacked, contiguous slices or sheets $OS_1$, $OS_2$, ..., $OS_k$, each of which contains the same number of object volume elements (voxels) OV. Each voxel has a rectangular profile in the sheet plane (say, the X-Y plane); while the complementary sides may be of equal length S, so that this profile may be square, the sheet thickness T is generally not equal to the length of either side. Thus, the first object slice $OS_1$ contains a first multiplicity of object voxels $OV_{i,j,1}$ where i and j are the respective X-axis and Y-axis positions of the voxel. Similarly, the second object slice $OS_2$ contains object voxels $OV_{i,j,2}$. An arbitrary object slice $OS_k$ contains voxels $OV_{i,j,k}$, where k is the Z-axis position of that voxel.

Each object voxel $OV_{i,j,k}$ is analyzed and the data value (intensity, velocity or power) thereof is placed in a corresponding data voxel $DV_{i,j,k}$ of a data volume 54. Data volume 54 is a simple cubic i,j,k lattice, even though the thickness of each object slice $OS_k$ and each object voxel face size (the size of the voxel in the X-Y plane) will generally not be the same. That is, not only may the object volume have different X, Y and Z dimensions for each voxel, but also the total number of voxels in any dimension need not be the same. For example, a typical ultrasound three-dimensional scan may provide each slice with a 256×256 matrix of voxels, and may involve 128 slices.

In accordance with a known technique employed by CPU 42, an image of object 50 is projected (step 34 in FIG. 3) by ray casting toward the image plane 56 from a lattice point in data voxel $DV_{i,j,k}$. For convenience, the lattice point may, for example, be the data voxel vertex closest to the data volume origin. The cast ray 17 leaves the data volume 54 at a projection angle with spherical angular parameters $(\alpha,\beta)$ transformed from the spherical angular parameters $(\theta,\phi)$ at which the object volume 52 is viewed. These two angles are not the same, due to the geometric distortion caused by use of a cubic data volume 54 with a non-cubic object volume 52. However, the projected ray 17 has an $\overline{X}$-$\overline{Y}$ plane extension 17' which makes an angle $\alpha$ with respect to the $\overline{X}$ axis of the data volume, and ray 17 makes an angle $\beta$ with the Z axis. Thus, angles $\alpha$ and $\beta$ are determined by a rotation process (to be discussed hereinbelow) to correspond to viewing the object volume 52 at the desired viewing angle $(\theta,\phi)$ (assuming operation in spherical coordinates). Each of the rays 17 is cast from the data volume voxel lattice point toward the image plane.

While all rays 17 impinge upon some portion of the image plane, only those rays falling within the image plane pixel 60a under consideration are allowed to contribute to the data for that image plane pixel. Thus, having chosen a portion of the object volume 52 to view and a viewing angle (θ,φ) at which to view this selected object volume, the data value in each voxel of the corresponding portion of the data volume is cast at some angle (α,β) (corresponding to viewing the distorted data volume with respect to the object volume) toward the image plane 56. The data value in a first voxel (say, voxel $DV_{i,1,k}$) is thus back-projected along ray 17a, in accordance with the θ and φ values chosen. This ray 17a impinges upon image plane 56 at a position 64a within pixel 60a, and, as this is the first ray to impinge upon this pixel, the intensity, velocity or power value of the incident data is attributed to (stored in) the desired pixel 60a. The next voxel in the data volume (say voxel $DV_{i,2,k}$) has its associated ray 17b projected at the same angular (α,β) configuration from the voxel lattice point, and its position 64b upon image plane 56 is noted. Assuming that impingement position 64b is within desired pixel 60a, the second projected value is (for a maximum pixel projection) compared with the now stored first value and the larger value is placed in storage for pixel 60a. It will be understood that, for an averaged-value projection, the value of a current projected data voxel is added to the sum already stored for the image panel pixel upon which that projection ray impinges, and the sum is eventually divided by a counted number of such impinging rays for that pixel. As each voxel in the selected data volume is sequentially entered and projected toward image plane 56, a data volume voxel (say, voxel $DV_{i,3,k}$) is eventually projected along its associated ray 17p and does not impinge within the desired pixel 60a, so that its data value (e.g., intensity) is not compared to the data value presently stored for pixel 60a. The maximum data value for pixel 60a is now established, for that projection of the data at the particular (θ,φ) three-dimensional angle of view. However, the ray 17p does, in fact, have an impingement point 64p which falls within another image plane pixel (say, pixel 60b) and is compared to the data value stored therein and the larger value is, after the comparison, returned to storage for that pixel. All data values are reset to zero when a new projection is to be taken. Thus, each of the image plane pixels is reset at the start of an image projection procedure, and all of the data volume voxels (in the entire space or in the selected portion, as set by the portion of the object volume 52 selected) are individually and sequentially scanned. The data value in each data voxel DV is projected through an associated ray 17 to impinge upon image plane 56 in one pixel 60 thereof, with the maximum value in each pixel being compared between the present value of the ray-casted data volume voxel, to determine the larger thereof, which larger value is then stored as part of the maximum value image. In practice, for a maximum pixel projection, the stored maximum value will be changed only if the newly cast data voxel value is greater than the data value already stored for the image plane pixel upon which the newly cast ray impinges.

Figure 5:
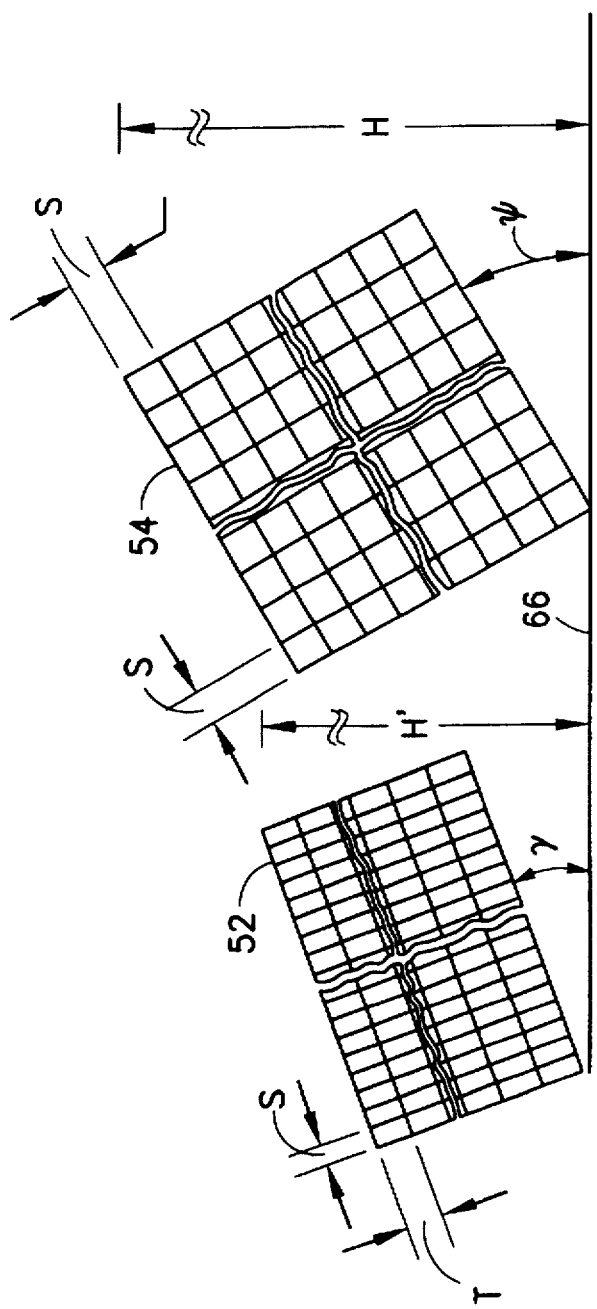
FIG. 5 is a schematic showing a pair of geometric two-dimensional configurations corresponding to like views of object and data volumes, and useful in defining necessary scaling constants in three-dimensional ultra-sound imaging.

In accordance with another aspect of the foregoing technique, the data projection is scaled (step 36 in FIG. 3) and any anisotropy between the object volume and the image plane is removed by only a single set of calculations after back projection is complete. Referring now to FIG. 5, because object volume 52 is a real volume while data volume 54 is an abstract concept, it is necessary to determine the amount of distortion of the data projection due to the presentation of the cubic data volume lattice 54 at a different angle γ, in a first plane, then the angle ψ at which an arbitrary viewing direction 66 will be positioned with respect to both the object volume 52 and data volume 54. The apparent dimensions of each voxel are going to change as the effective elevation angles ψ and γ change. If the aspect ratio A (defined as the ratio of the actual slice thickness T in object volume 52 to the actual pixel size S in the same object volume 52) is not unity (i.e., is greater or less than unity, as the object voxel is not a cubic voxel, as will be encountered in data volume 54), then the angles ψ and γ of elevation will be different, and the effective elevation angle ψ in the data volume will be different than the actual elevation angle γ in the object volume. Rotation of the data is in accordance with an object elevation angle obtained by:

$$\psi = \tan^{-1}\left(\frac{1}{A}\tan|\gamma|\right)$$

Thereafter, the projected data can be scaled to have the correct height (if rotation is about the horizontal axis) in the object volume, by multiplication of all projected data heights by the elevation scale factor. The old projected image height H can be corrected with an effective scale factor $E_s$, where $$E_s = \sqrt{(A\cos\gamma)^2 + \sin^2\gamma}$$

and the new height H'=H·$E_s$. The same is true for the width when rotation is about the vertical axis.

Utilizing the above relationship, the rotation of data volume angles (α,β) becomes angles (θ,φ), because the distortion is only along one axis, so that angle θ equals angle α. The elements of the 3×3 rotational matrix |M| can be determined, and given the two involved rotational angles, these relationships are used to determine the data volume-to-image plane transformations:

$$X'=M1X+M2Y+M3Z+XO$$

$$Y'=M4X+M5Y+M6Z+YO$$

where M1–M6 are the first two rows of the rotational matrix (i.e., M1=−sin θ, M2=cos θ sin ψ, M3=0, M4=−cos θ sin ψ2, M5=−sin θ sin ψ, and M6=cos ψ), X' and Y' are the locations on the image plane of the projected point, and XO and YO are image plane X and Y offsets (respectively referenced to the X and Y lowest value points) at which the selected portion of the image plane begins. After the data is projected onto image plane 56, the image is scaled to correct for the effect of the anisotropic object voxels. It will be seen that factors M1–M6 can be precalculated (step 32 in FIG. 3) at the beginning of a projection (given θ and φ) and used for all rotation calculations.

Figure 6:
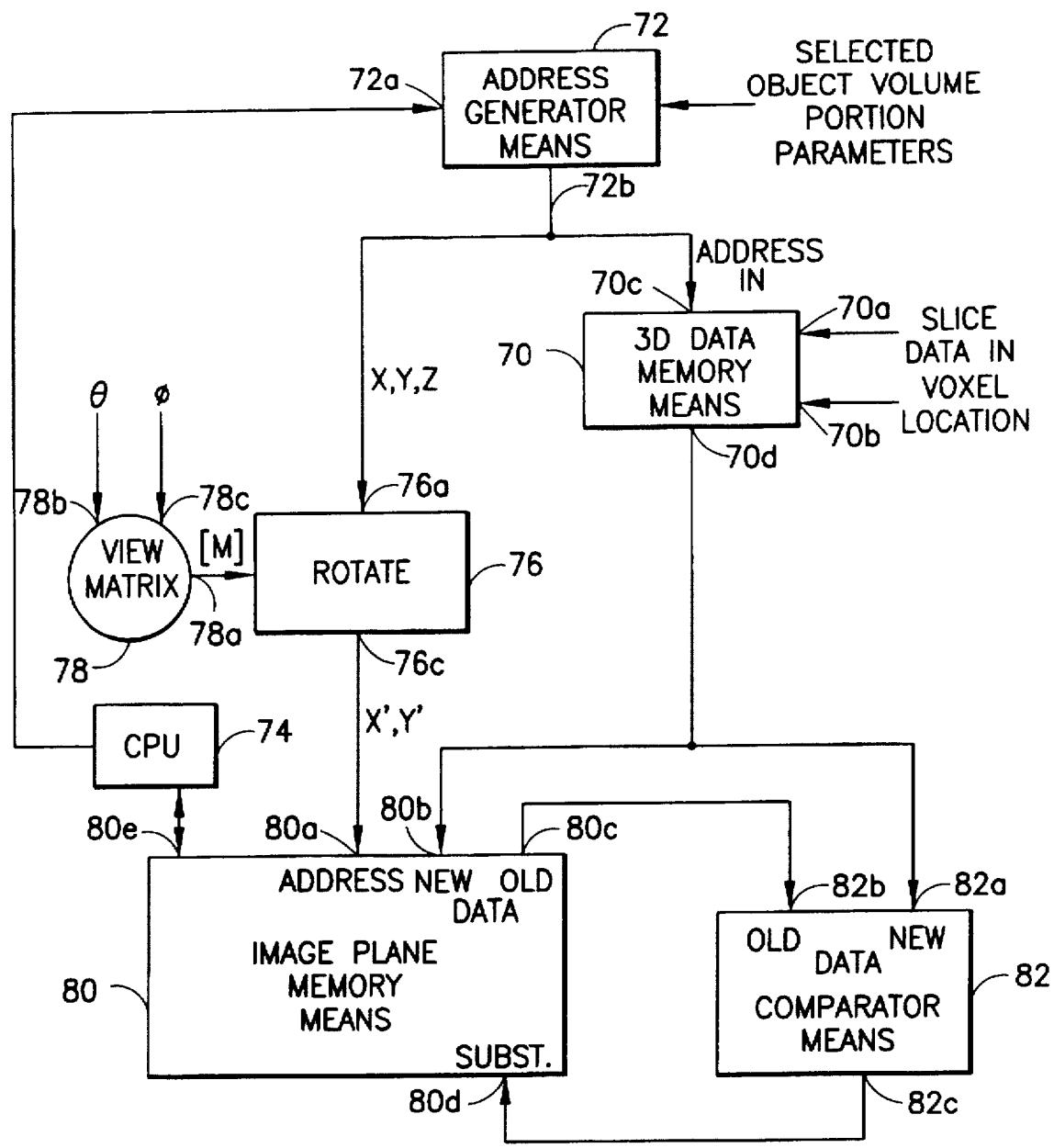
FIG. 6 is a schematic block diagram of means for providing a maximum intensity projection in three-dimensional ultrasound imaging.

FIG. 6 shows means for performing the above-described ray-casting technique which are incorporated in the master controller 8 (or a separate dedicated processor). Such means comprise a three-dimensional data memory means 70 for storing slice data as received at a data input 70a from cine memory 24. The data associated with each object voxel is stored at the address of that voxel, responsive to voxel address input information received at a voxel address input 70b from a CPU 74. Once the data memory means is filled (corresponding to the transfer of all required data from object volume 52 to data volume 54), the object volume portion of interest is selected and data establishing its starting corner and extent in the X, Y and Z directions is sent from CPU 74 to an input 72a of an address generator means 72. Means 72 sequentially provides, at an address output 72b, the X,Y,Z addresses of each voxel within the object volume selected. Output 72b is connected to an output-data-address input 70c of data memory means 70, causing the stored intensity data for that one voxel then addressed to be output from data memory means output 70d. The sequence of voxel X,Y,Z addresses is also provided to a first input 76a of a rotational parameter calculation means 76, which receives angle ($\alpha,\beta$) information via CPU 74 as the calculated matrix element M1–M6 values, to provide at an output 76c the address X',Y' of the image plane pixel corresponding to that object X,Y,Z pixel when viewed at a selected viewing angle ($\theta,100$ ). The viewing angle ($\theta,\phi$) information is entered into the system and processed by CPU 74. The results are entered into inputs 78b and 78c of a viewing matrix means 78, to provide matrix elements M1–M6 at its output 78a and thence to rotational parameter calculation means 76. The image plane pixel address X',Y' appears at an address input 80a of a frame buffer acting as an image plane memory means 80. Simultaneously, the intensity data, projected from the data volume to the projection plane, appears at the image plane memory means new data input 80b, from three-dimensional data memory means output 70d. This data also appears at the new data input 82a of a data comparator means 82. Intensity data previously saved in the image plane memory means 80 for that address, at input 80a, appears at an old data output 80c, and thence at an old data input 82b of the comparator means. The old and new data at inputs 82b/82a, respectively, are compared in means 82 and an output 82c thereof is enabled to a selected logic condition (e.g., a high logic level) if the new data at input 82a has greater amplitude than the old data at input 82b. Output 82c is connected to a substitute-control data input 80d of the image plane memory means, to cause the data stored at the address controlled by input 80a to be changed to accept the new data at input 80b, if the substitute-data control input 80d is at the selected logic level. Thus, the stored data is initially reset, as by a signal through a data/control port 80e (from CPU 74), and the data of greatest value is stored for each image plane pixel location X',Y' responsive to a comparison indicating that the new data exceeds the value of the previously stored old data. After all of the selected addresses are sequentially scanned by address generator 72, the data stored in image plane memory means 80 is scaled in CPU 74, and the scaled image plane data can be withdrawn from memory means 80 for display, permanent storage or similar purposes.

In accordance with a further aspect of the invention, prior to display the scaled image plane data is mapped to achieve a desired brightness and contrast range (step 38 in FIG. 3). While reading in the region of interest for the source frames on which the three-dimensional reconstruction is based, a histogram of the number of pixels with a given intensity is optionally created in the master controller 8. Alternatively, the histogram can be formed using the projected images. At the same time, the maximum pixel intensity is determined. The pixels in each bin are counted until a given percentage of the total number of pixels is reached. This bin number becomes the pixel threshold. A map is then created such that each pixel value is mapped to the desired brightness and contrast range above or below the pixel threshold depending on the intended result.

Figure 1:
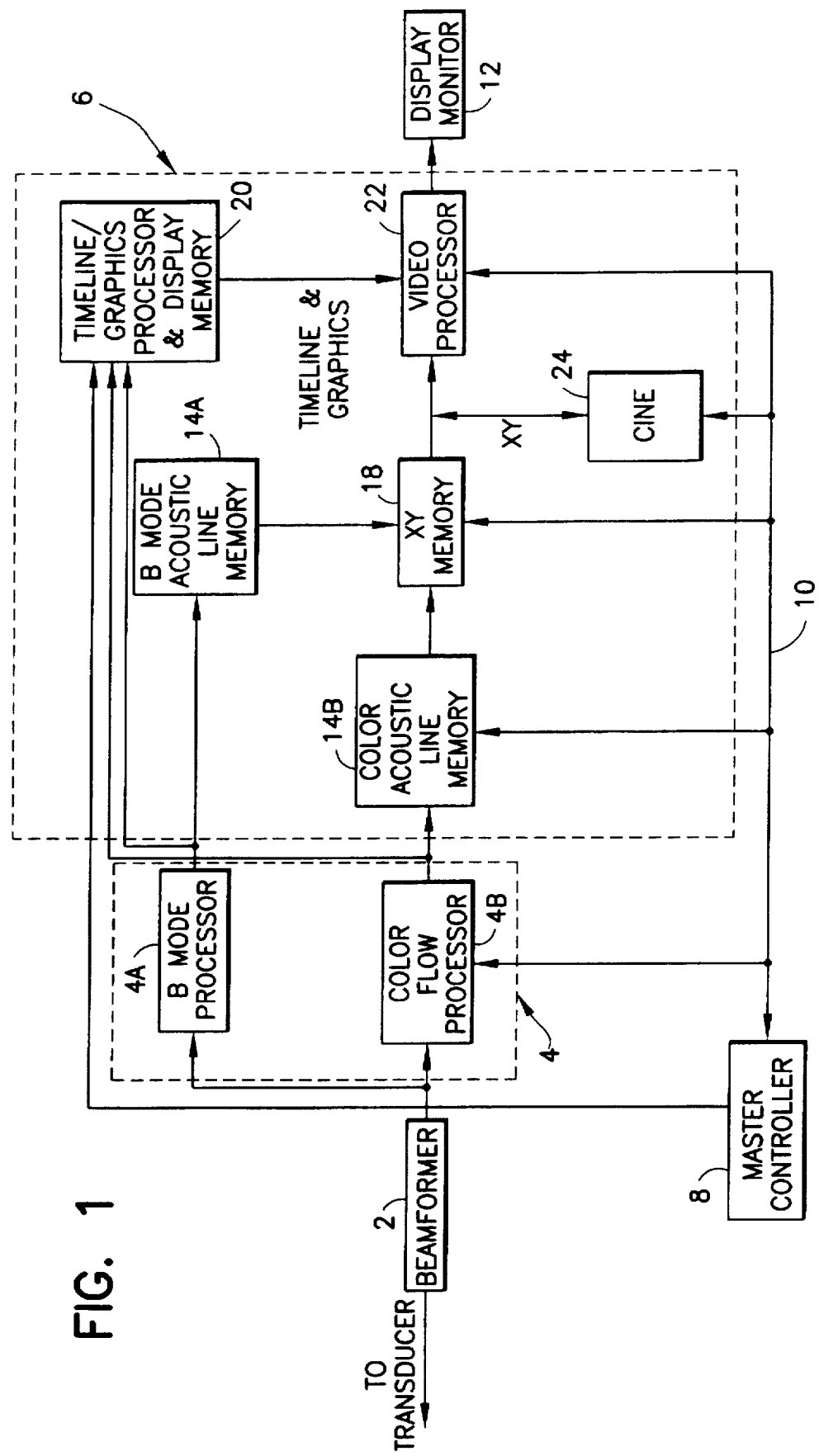
FIG. 1 is a block diagram showing the major functional subsystems within a real-time ultrasound imaging system.

In accordance with the present invention, the pixels in the region of interest from each slice or frame stored in the cine memory 24 (see FIG. 1) are convolution filtered by the CPU 42 and then stored in memory 44 (see FIG. 2). The region-of-interest pixels stored in the cine memory can be read therefrom and supplied to the convolution filter as successive pixels or as an array of pixels. The operations performed by the convolution filter incorporated in CPU 42 will be described in greater detail with reference to FIG. 8.

The apparatus in accordance with the invention comprises a convolution filter having a multiplicity of taps for receipt of a respective multiplicity of weighting coefficients. This set of weighting coefficients may be stored in random only memory 44 and retrieved from memory by CPU 42. Multiple sets of weighting coefficients could be stored as a lookup table in memory 44, with one set being retrieved in response to a selection made by the system operator. In accordance with the preferred embodiment, the number of weighting coefficients in the set equals nine, each of which may be represented as a multi-bit (e.g., 8-bit) digital number. The nine weighting coefficients ($W_1$ through $W_9$ in FIG. 7B) are arranged as a 3×3 kernel which is effectively moved through the entire pixel region of interest such that the center point of the kernel is stepped down each range vector in sequence (excluding the first and last range vectors and excluding the first and last data points of each vector).

For example, referring to FIG. 7A, the 9-point kernel (see FIG. 7B) is moved down range relative to the first three vectors, namely, $DV_{4,4,1}$-$DV_{4,1,1}$, $DV_{3,4,1}$-$DV_{3,1,1}$ and $DV_{2,4,1}$-$DV_{2,1,1}$, so that these first three vectors of pixel data are processed to form a first new filtered vector, which is stored at another location. In the first filtering operation, the weighting coefficients are applied to the 3×3 array of pixels in the upper left-hand corner of the array shown in FIG. 7A. Weighting coefficient $W_1$ is used to weight pixel $DV_{4,4,1}$; weighting coefficient $W_2$ is used to weight pixel $DV_{3,4,1}$; weighting coefficient $W_3$ is used to weight pixel $DV_{2,4,1}$; weighting coefficient $W_4$ is used to weight pixel $DV_{4,3,1}$; and so on. The convolution filter produces a processed (i.e., filtered) pixel which is substituted for the pixel $DV_{3,3,1}$. This filtered pixel $DV_{3,3,1}^{fil}$ may be calculated as follows:

$$DV_{3,3,1}^{fil} = DV_{4,4,1} \cdot W_1 + DV_{3,4,1} \cdot W_2 + DV_{2,4,1} \cdot W_3 +$$
$$DV_{4,3,1} \cdot W_4 + DV_{3,3,1} \cdot W_5 + DV_{2,3,1} \cdot W_6 +$$
$$DV_{4,2,1} \cdot W_7 + DV_{3,2,1} \cdot W_8 + DV_{2,2,1} \cdot W_9$$

Thus, the filtered pixel produced by the convolution filter is the sum of the 3×3 pixels, which include the pixel being processed and the surrounding pixels, each of these pixels being weighted by a respective one of the weighting coefficients $W_1$–$W_9$. In the next stage, the 9-point kernel in FIG. 7B is applied to the 3×3 pixel array in the lower left-hand corner of the array in FIG. 7A, to obtain $DV_{3,2,1}^{fil}$. In this simplified example, the pixels $DV_{3,3,1}^{fil}$ and $DV_{3,2,1}^{fil}$ form the first new filtered vector. For a column having more than five pixels, this process is repeated until the penultimate pixel in the column has been filtered. Thereafter, the second ($DV_{3,4,1}^{fil}$-$DV_{3,1,1}$), third ($DV_{2,4,1}$-$DV_{2,1,1}$) and fourth ($DV_{1,4,1}$-$DV_{1,1,1}$) adjacent vectors of pixel data are processed to form a second new filtered vector, which will be stored adjacent to the first new filtered vector. This process is repeated until a new set of filtered vectors, forming a new filtered pixel image, has been acquired and stored in a new location.

If the source data comprises intensity data and velocity or power Doppler data, the aforementioned convolution filtering operation may be carried out separately for each component.

In accordance with the preferred embodiment of the present invention, the weighting coefficient $W_5$=4, while the other eight weighting coefficients are equal to unity. Such a convolution filter may be implemented as shown in FIG. 8, although it is understood by practitioners skilled in the art of digital filtering that other implementations could be used.

Referring to FIG. 8, the convolution filter can be schematically represented as comprising a multiplicity of pixel delay elements 86a–86i, a multiplicity of multipliers 88a–88i, and a multiplicity of adders 90a–90i. The pixel delay elements are connected as banks of shift registers, each delay element being adapted to store a pixel value for a period of time equal to the rate at which pixels are read out of memory 44 (see FIG. 1). Pixel delay elements 86a–86c are connected as one shift register; pixel delay elements 86d–86f are connected as another shift register; pixel delay elements 86g–86i are connected as a third shift register. These shift registers are used to provide a 3×3 pixel array to multipliers 88a–88i.

The shift register comprised of pixel delays 86a–86c is connected to receive successive pixels directly from memory 44. The shift register comprised of pixel delays 86d–86f is connected to a line memory 82 which, in turn, is supplied with successive pixels read from memory 44. Line memory 82 imparts a delay equal to one horizontal line interval to the pixels supplied from memory 44. Likewise, the shift register comprised of pixel delays 86g–86i is coupled to a line memory 84 which, in turn, is connected in cascade with line memory 82 and imparts a delay equal to one horizontal line interval to the pixels that have already been delayed by line memory 10. Thus, line memories 82 and 84 cause a particular pixel in one horizontal line to be in time coincidence with the pixels in the same column but in the two preceding lines. For example, referring to FIG. 7A, it will be seen that, when pixel $DV_{3,2,1}$ is provided from memory 44, pixel $DV_{3,3,1}$ is provided at the output of line memory 82 and pixel $DV_{3,4,1}$ is provided at the output of line memory 84.

Multiplier 88a receives the weighting coefficient $W_1$ and the pixel data value output by delay element 86a and forms the product of these inputs. Similarly, multiplier 88b receives the weighting coefficient $W_2$ and the pixel data value output by delay element 86a and forms the product of these inputs. Nine products are produced using the nine weighting coefficients and the nine pixels data values comprising the 3×3 array being processed. These nine products are summed by adders 90a–90h to form a new filtered pixel data value. The convolution filter operates continuously until a new filtered frame of pixel data has been acquired.

The present invention is not limited to use of convolution filtering. Alternatively, the pixel data can be filtered using a median filter or an edge-preserving filter.

The projection technique is separately applied to the B-mode intensity data and to the color flow velocity or power data for the data volume of interest retrieved from the cine memory. Each pixel in the projected image includes the transformed intensity data and the transformed velocity or power data derived by projection onto a given image plane. In addition, at the time when the cine memory was frozen by the operator, the CPU 42 optionally stores the last frame from the XY memory 18 at multiple successive addresses in section 24B of cine memory 24. The projected image data for the first projected view angle is written into the first address in cine memory section 24B, so that the projected image data in a region of interest is superimposed on the background frame. This process is repeated for each angular increment until all projected images are stored in cine memory section 24B, each projected image frame consisting of a region of interest containing transformed data and optionally a background perimeter surrounding the region of interest consisting of background frame data not overwritten by region-of-interest transformed data. The background image makes it clearer where each displayed projection is viewed from. The operator can then select any one of the projected images for display. In addition, the sequence of projected images can be replayed on the display monitor to depict the object volume as if it were rotating in front of the viewer.

In accordance with a preferred embodiment of the invention, the ultrasound imaging system has a plurality of different projection modes. For example, the projection may include maximum or minimum value pixels. Alternatively, a mode useful in imaging blood vessels may be selected wherein the pixel data is inverted and then the maximum values are projected onto the image plane. In accordance with a further mode, the ray-casting technique can be employed to provide a surface rendering.

The foregoing preferred embodiment has been disclosed for the purpose of illustration. Variations and modifications of the basic concept of the invention will be readily apparent to those skilled in the arts of ultrasound imaging or computer graphics. All such variations and modifications are intended to be encompassed by the claims set forth hereinafter.

We claim:

1. A system for three-dimensional imaging of ultrasound scatterers in an object volume, comprising:

an ultrasound transducer array for transmitting ultrasound beams and detecting ultrasound echoes reflected from said object volume at a multiplicity of focal positions in a scan plane;

means coupled to said ultrasound transducer array for acquiring imaging data derived from ultrasound echoes reflected from each one of a multiplicity of scan planes through said object volume;

means for converting the acquired imaging data for each scan plane into a respective image frame of pixel data;

memory means for storing pixel data for each of a multiplicity of image frames corresponding to said multiplicity of scan planes;

means for retrieving a volume of pixel data from said memory means corresponding to a volume of interest in the object volume;

means for three-dimensional filtering said volume of pixel data by applying a set of filter coefficients to pixel data of n image frames during each filtering operation, where n≧2, to form a three-dimensionally filtered pixel data volume;

means for projecting said three-dimensionally filtered pixel data volume onto a first image plane, thereby forming a first projected data set representing a first projected image;

a display monitor; and means for displaying said first projected image on said display monitor.

2. The system as defined in claim 1, wherein said projecting means comprise means for performing maximum pixel projections.

3. The system as defined in claim 1, wherein said projecting means comprise means for performing minimum pixel projections.

4. The system as defined in claim 1, wherein said three-dimensional filtering means comprise a convolution filter.

5. The system as defined in claim 1, wherein said pixel data comprises intensity data.

6. The system as defined in claim 1, wherein said pixel data comprises flow velocity data.

7. The system as defined in claim 1, wherein said pixel data comprises flow power data.

13

8. The system as defined in claim 1, further comprising:

means for projecting said three-dimensionally filtered pixel data volume onto a second image plane which is rotated relative to said first image plane, thereby forming a second projected data set representing a second projected image; and means for displaying said second projected image on said display monitor.

9. A system for three-dimensional imaging of ultrasound scatterers in an object volume, comprising:

an ultrasound transducer array for transmitting ultrasound beams and detecting ultrasound echoes reflected from said object volume at a multiplicity of focal positions in a scan plane;

means coupled to said ultrasound transducer array for acquiring imaging data derived from ultrasound echoes reflected from each one of a multiplicity of scan planes through said object volume;

means for converting the acquired imaging data for each scan plane into a respective image frame of pixel data;

frame memory means for storing an image frame of pixel data for each of said multiplicity of scan planes;

cine memory means for storing a multiplicity of image frames of pixel data output in succession by said frame memory means;

means for retrieving a volume of pixel data from said cine memory means corresponding to a volume of interest in the object volume;

means for three-dimensional filtering said volume of pixel data by applying a set of filter coefficients to pixel data of n image frames during each filtering operation, where $n \geq 2$, to form a three-dimensionally filtered pixel data volume;

means for projecting said three-dimensionally filtered pixel data volume onto first and second image planes, thereby forming first and second projected data sets representing first and second projected images, respectively;

means for storing said first and second projected data sets in said cine memory means;

means for selecting one of said first and second image planes;

a display monitor; and means for displaying one of said first and second projected data sets corresponding to said selected one of said first and second image planes.

10. The system as defined in claim 9, wherein said three-dimensional filtering means comprise a convolution filter.

11. A method for three-dimensional imaging of ultrasound scatterers in an object volume, comprising:

14

(a) transmitting a multiplicity of ultrasound beams focused at respective transmit focal positions in a scan plane;

(b) detecting ultrasound echoes reflected from the ultrasound scatterers at said respective transmit focal positions in said scan plane;

(c) acquiring imaging data derived from said detected ultrasound echoes in said scan plane;

(d) converting the acquired imaging data for said scan plane into an image frame of pixel data;

(e) repeating steps (a) through (d) to form a multiplicity of image frames of pixel data for a respective multiplicity of scan planes intersecting the object volume;

(f) storing pixel data for each of said multiplicity of image frames;

(g) retrieving a volume of pixel data from said stored pixel data corresponding to a volume of interest in the object volume;

(h) three-dimensional filtering said pixel data volume by applying a set of filter coefficients to pixel data of n image frames during each filtering operation, where $n \geq 2$, to form a three-dimensionally filtered pixel data volume;

(i) projecting said three-dimensionally filtered pixel data volume onto a first image plane, thereby forming a first projected data set representing a first projected image; and (j) displaying said first projected image.

12. The method as defined in claim 11, wherein said projecting step comprises the steps of performing maximum pixel projections.

13. The method as defined in claim 11, wherein said projecting step comprises the steps of performing minimum pixel projections.

14. The method as defined in claim 11, wherein said step of three-dimensional filtering comprises convolution filtering.

15. The method as defined in claim 11, wherein said pixel data comprises intensity data.

16. The method as defined in claim 11, wherein said pixel data comprises flow velocity data.

17. The method as defined in claim 11, wherein said pixel data comprises flow power data.

18. The method as defined in claim 11, further comprising the steps of:

projecting said three-dimensionally filtered pixel data volume onto a second image plane which is rotated relative to said first image plane, thereby forming a second projected data set representing a second projected image; and displaying said second projected image.

* * * * *